United States Patent [19]
Kuraishi et al.

[11] Patent Number: 5,681,598
[45] Date of Patent: Oct. 28, 1997

[54] PROCESS FOR PRODUCING CHEESE USING TRANSGLUTAMINASE

[75] Inventors: Chiya Kuraishi; Jiro Sakamoto; Takahiko Soeda, all of Kawasaki, Japan

[73] Assignee: Ajinomoto Co., Inc., Tokyo, Japan

[21] Appl. No.: 548,681

[22] Filed: Oct. 26, 1995

[30]     Foreign Application Priority Data

Oct. 26, 1994 [JP] Japan .................................. 6-262117
Jun. 1, 1995 [JP] Japan .................................. 7-134947

[51] Int. Cl.$^6$ ........................................................ A23C 9/12
[52] U.S. Cl. ........................ 426/36; 426/34; 426/38; 426/580; 426/582
[58] Field of Search ................................. 426/36, 38, 34, 426/582, 39, 40, 42, 43, 52, 580

[56]          References Cited

U.S. PATENT DOCUMENTS 5,055,310  10/1991  Nonaka et al. .
5,156,956  10/1992  Motoki et al. ........................ 426/573

FOREIGN PATENT DOCUMENTS 379 606    8/1990   European Pat. Off. .
93/22930   11/1993  WIPO .
94/21129   9/1994   WIPO .
94/21130   9/1994   WIPO .

*Primary Examiner*—Leslie Wong
*Attorney, Agent, or Firm*—Oblon, Spivak, McClelland, Maier & Neustadt, P.C.

[57]            ABSTRACT

The present invention relates to a process for producing natural cheese, characterized in that a transglutaminase is included therein for a reaction. The process can provide a large amount of cheese curd compared to conventional methods, making it possible to efficiently use the starting milk. Further, the obtained cheese has an excellent flavor, texture and appearance.

9 Claims, No Drawings

1

PROCESS FOR PRODUCING CHEESE USING TRANSGLUTAMINASE

FIELD OF THE INVENTION

The present invention relates to a process for producing cheese, and more specifically, it relates to a process for producing cheese using an enzyme, transglutaminase (hereinafter abbreviated as "TG").

DISCUSSION OF THE BACKGROUND

Natural cheese (the term "cheese" refers to natural cheese hereinafter unless otherwise indicated) was once only scarcely familiar to the Japanese people, but in recent years, various kinds of cheese have become obtainable. It has been said that there are approximately 400 kinds of cheese which are usually eaten in foreign countries but most are unfamiliar in Japan.

In the production of cheese, it is industrially preferable to form a curd in as large an amount as possible from a fixed amount of starting milk, in view of the production costs and the effective application of milk resources and because the product can be distributed to consumers at low cost.

However, having obtained a high yield of curd in the conventional method of producing cheese means, in many cases, that the whey drainage was not satisfactory. As a result, properties of cheese, such as firmness, body, texture and the like are lost, thereby making the quality of the cheese low level.

Attempts have been made to improve the yield of the curd by utilizing a whey protein in the production of cheese. For example, U.S. Pat. No. 4,205,090 describes a method in which milk is concentrated to a volume of approximately ⅓ through ultrafiltration, and cheese is produced using this concentrated milk as a starting material. Japanese unexamined Patent publication of PCT application (Kohyou) No. 501,810/1982 describes a method in which cheese is produced from a substance, as a starting material, which is obtained by selectively concentrating milk through ultrafiltration, increasing the ion intensity of the concentrate, then fermenting the concentrate and removing the water therefrom. Japanese Laid-Open Patent Application (Kokai) No. 308,756/1990 describes that when cheese is produced using a concentrated starting raw milk and a protein of a concentrated whey which is obtained by concentrating the whey formed as a by-product in the production of cheese, the whey protein is contained in the obtained cheese curd at a high concentration, and as a result, the whey protein formed as a by-product can thus be effectively utilized.

However, in these methods, the starting milk or the whey to be reused has to be subjected to a pre-treatment such as concentration through ultrafiltration or the like. Accordingly, it is considered that these methods are neither industrially simple, nor is the quality of cheese produced satisfactory enough to the consumers.

The following documents have already reported milk products using TG. Japanese Laid-Open Patent Application (Kokai) No. 27,471/1989 (The corresponding is U.S. Pat. No. 5,156,956 and the corresponding European Patent No. under EPC is 0379606 B.) describes a method of producing cheese which includes a step of adding TG during the production. However, the cheese described in Japanese Laid-Open Patent Application (Kokai) No. 27,471/1989 is produced from a curd which is obtained using glucodeltalactone and TG or TG alone but not a rennet (milk clotting enzyme), and this method is vastly different from the process for producing cheese using the milk-clotting enzyme in the present invention.

Japanese Laid-Open Patent Application (Kokai) No. 131,537/1990 involves a method of producing a cheese food using TG. However, the cheese food intended here is produced by heat-melting natural cheese or process cheese as a starting material. Thus, "cheese food" is classified as a food which is very different from natural cheese intended in the process of the present invention. The cheese food described above is classified as "process cheese preparation" according to the international standard of FAO/WHO.

WO 93/19610 describes a method in which a milk protein solution of which the pH is adjusted in the acidic region by means of a yogurt starter is reacted with TG. However, the above-mentioned invention does not include a step of adding a milk-clotting enzyme and defines a final product, strictly speaking, as a milk-like product which is different from what the present invention terms "cheese."

WO 94/21129 describes a method of producing an acidic edible gel based on milk and the application of the edible gel produced by this method to cheese. However, the above-mentioned invention does not have any description about addition of a milk clotting enzyme. Accordingly, this method is quite different from the process for producing cheese in the present invention wherein the milk clotting enzyme is added for a reaction. Further, cheese using the edible gel is extremely different from the natural cheese intended in the present invention.

On the other hand, the following documents report milk products using TG and a milk clotting enzyme.

WO 93/22930 describes a method in which a solution containing a milk protein is reacted with TG to produce a milk-like product. However, there is nothing in the above-mentioned document to describe the production of cheese itself. Further, a method of producing a milk-like product as described in the Examples of this document is vastly different from the process for producing cheese using the milk clotting enzyme in the present invention, and the final product is not cheese itself. Still further, this document does not disclose, at all, the order in which the treatments with TG and the milk clotting enzyme are to be conducted, however, as is mentioned in the present invention.

WO 94/21130 describes a method of producing a non-acidified edible gel based on milk, which comprises reacting a milk protein solution with TG at a first stage, adding a rennet (milk clotting enzyme) to the mixture for a reaction at a second stage, and heat-treating the reaction mixture at a third stage. It also indicates the use of the thus-obtained edible gel for cheese. However, the order of the addition of the rennet (milk clotting agent), the addition of TG and the heat treatment is clearly different from the order provided in the present invention.

WO 93/22930 and WO 94/21130 do not have any description regarding a step for decreasing the pH with the addition of a cheese starter. In this respect as well, the methods disclosed in these documents no doubt differ from the process for producing cheese, namely, natural cheese using a cheese starter in the present invention.

WO 94/21130 indicates that the rennet (milk clotting enzyme) added does not exhibit ordinary performance (separation of milk into cheese curd and whey) and forms a single-phase gel. Even if such a gel is used in cheese, it is wholly different from cheese which is produced through a step of discharging whey like ordinary natural cheese.

The present inventors have assiduously conducted investigations to solve the above-mentioned problems, and have discovered that when TG catalyzes an acyl transfer reaction between the γ-carboxyamide group of a glutamine residue and a primary amine in a protein or a peptide chain, and furthermore the primary amine is a lysine residue of a protein, an ε-(γ-Glu)-Lys crosslink is formed. As a result, we have found that when steps of adding TG and a milk clotting enzyme for a reaction are incorporated under suitable conditions and in suitable order, the weight of the curd formed is clearly increased, and the obtained curd is transformed into cheese which has good quality even after it is matured while maintaining the necessary firmness and good body. This finding has led to the completion of the present invention.

SUMMARY OF THE INVENTION

One object of the invention is to provide a process for producing cheese, which comprises (1) adding a transglutaminase to a solution containing milk or a milk protein for a reaciton at a first stage, (2) heat-treating the mixture at a second stage, and (3) adding a milk clotting enzyme at a third stage to react the mixture with the milk clotting enzyme for a fixed period of time.

Another object is to provide a process for producing cheese, which comprises (1) adding a milk clotting enzyme to a solution containing milk or a milk protein at a first stage to react the solution with the enzyme for a fixed period of time, and then (2) adding a transglutaminase to the mixture for a reaction at a second stage.

Another object is to provide a process for producing cheese, which comprises adding a transglutaminase to a solution containing milk or a milk protein for a reaction and, at the same time, a milk clotting enzyme is added to the solution.

DETAILED DESCRIPTION OF THE PREFERRED EMBODIMENTS

The present invention relates to (1) a process for producing cheese, which comprises adding TG to a solution containing milk or a milk protein for a reaction at a first stage, heat-treating the mixture at a second stage, and adding a milk clotting enzyme at a third stage to react the mixture with the milk clotting enzyme for a fixed period of time, (2) a process for producing cheese, which comprises adding a milk clotting enzyme to a solution containing milk or a milk protein at a first stage to react the solution with the enzyme for a fixed period of time, and then adding TG to the mixture for a reaction at a second stage, and (3) a process for producing cheese, which comprises adding TG to a solution containing milk or a milk protein for a reaction at the same time as a milk clotting enzyme is added to the solution. Japanese patent applications 262117/1994 and 134947/1995 are incorporated herein in their entirety.

What the present invention terms "cheese" refers to natural cheese, and the process for producing cheese includes a step of "acidification" in which a starter is added to starting milk and a step of "rennetting" by action of a milk clotting enzyme. There are a great many kinds of cheese. The process of the present invention is directed to all kinds of cheese which are produced by a process including acidification with a starter and a rennetting.

The present invention is characterized in that the step of adding TG for a reaction is incorporated into the production of all kinds of cheese in a suitable order. The step of adding TG for the reaction is incorporated according to the following three preferred processes.

The first process comprises three stages, that is, adding TG to a solution containing milk or a milk protein at a first stage, heating the mixture at a second stage, and adding a milk clotting enzyme to the reaction mixture at a third stage to react the reaction mixture with the milk clotting enzyme for a fixed period of time.

The second process comprises adding a milk clotting enzyme to a solution containing milk or a milk protein at a first stage to react the solution with the enzyme for a fixed period of time, and then adding TG to the reaction mixture for a reaction at a second stage.

The third process comprises adding TG to a solution containing milk or a milk protein for a reaction at the same time as a milk-clotting enzyme is added to the solution.

The conventional method of producing cheese can be applied except for the above-mentioned incorporation of the step of adding TG for the reaction and the order of that step.

TG which is used in the present invention may be derived from any source so far as it exhibits TG activity. Examples of TG include TG derived from microorganisms belonging to the genus *Streptoverticillium* and the like, hereinafter abbreviated as "BTG"; Japanese Laid-Open Patent Application (Kokai) No. 27,471/19891), TG derived from mammals such as guinea pigs (hereinafter abbreviated as "MTG"; to Japanese Patent 2nd. Publication (Kokoku) No. 50,382/1989), TG derived from fish such as a cod and the like (Seki Nobuo et al., "Bulletin of the Japanese society of Scientific Fisheries", vol. 56, No. 1, p. 125 (1990)), and TG which is obtained through gene recombination (Japanese Laid-Open Patent Application (Kokai) Nos. 300.889/1989, 199,883/1993 and 225,775/1994). Of these, BTG is preferable because it acts in the absence of calcium and can be obtained in large amounts.

The concentration of added TG is usually between 0.1 U and 50 U, preferably between 0.5 U and 10 U per gram of a cheese protein material. When the concentration of TG is lower than 0.1 U, the effect expected by the use of TG is not obtained. When it is higher than 50 U, TG acts excessively. As a result, milk proteins are aggregated excessively, the gel structure of the curd is destroyed, the amount of the curd obtained is decreased, and the resulting cheese is crumbly, making it hard to obtain a block of cheese.

Further, the addition of TG higher than 50 U leads to the undesirable effect that (1) the cheese is not smooth on the tongue, and (2) the cheese obtained as a final product does not have good taste. When cheese is produced according to the present invention, it is important to control the amount of TG used for obtaining the desired effects.

TG activity in the present invention is determined and defined as follows. A reaction system containing benzyloxycarbonyl-L-glutamylglycine and hydroxylamine as substrates is reacted with TG in a tris buffer (pH 6.0) at a temperature of 37° C., and the hydroxamic acid formed is transformed into an iron complex in the presence of trichloroacetic acid. Then, the absorbance at 525 nm is measured, and the amount of hydroxamic acid is calculated using a calibration curve. Thus, the amount of enzyme by which 1 μmol of hydroxamic acid is formed in 1 minute is defined as 1 unit (1 U) which is a unit of TG activity (Japanese Laid-open Patent Application (Kokai) No. 27,471/1989, U.S. Pat. No. 5,156,956, European Patent No. 0379606 B).

The processes in which TG is added to cheese in the present invention will be described in detail below.

When cheese is produced in accordance with the present invention, it is important to incorporate the step of adding TG for the reaction. As mentioned above, there are the three processes. When the present invention is conducted, the most suitable process may be selected from these three processes depending on the kind of cheese to be produced, the limitation of the production line and the like.

In the first process, TG is added to a solution containing milk or a milk protein at a first stage, the mixture is heat-treated at a second stage, and a milk clotting enzyme is added to the reaction mixture at a third stage to react the reaction mixture with the milk clotting enzyme for a fixed period of time. According to this process, the heat treatment is conducted after the solution is reacted with TG. Therefore, the TG added is deactivated, and, advantageously, no TG activity is left in the final product. At this time, the conditions for the heat treatment are not particularly limited. The heat treatment is usually conducted at from 72° to 75° C. for from 15 seconds to 2 minutes. It is considered that if TG activity remains in the final product in the case of the maturing of the cheese over a long period of time, it may be often that the properties of the cheese are changed during storage. However, when the process includes the step of deactivating TG through heating as mentioned above, such a change during storage can be avoided.

In the second process, a milk clotting enzyme is added to a solution containing milk or a milk protein at a first stage to react the solution with the enzyme for a fixed period of time, and then TG is added to the reaction mixture for a reaction at a second stage. The second process is, unlike the first process, characterized in that the solution containing milk or the milk protein is first reacted with the milk clotting enzyme, and the reaction mixture is then reacted with TG which is an enzyme to crosslink and polymerize the protein. In some kinds of cheese, this order sometimes exhibits the effect of the present invention remarkably.

In the third process, TG is added to a solution containing milk or a milk protein for a reaction at the same time a milk clotting enzyme is added to the solution. When the above-mentioned first and second processes cannot be adopted in view of the limited conditions for the production, cheese may be produced through the third process. This process in which TG is added simultaneously with the addition of the milk clotting enzyme is advantageous in that the change in conventional production steps is minimized and the step of adding TG is incorporated therein.

In the second and third processes, TG activity is left in the curd formed. In a fresh-type cheese which is stored for a short period of time, the change in the properties of cheese during storage is little. Even if the TG activity is left in the product which is distributed after the heat treatment of the final product, it poses no problem.

The means for adding TG is not particularly limited except that the step of adding TG for the reaction is incorporated according to any of the above-mentioned three processes. Examples of the milk clotting enzyme include animal rennets such as a calf rennet and a swine pepsin, plant rennets and microorganism rennets.

The animal rennets are preferable. Rennets which are produced through genetic engineering are also available.

When the starting milk is reacted with TG according to the process of the present invention, various additives can be used in order to make TG exhibit the more desired effect. For example, calcium chloride may be added to expedite the formation of the curd in the rennetting step.

In the present invention, cheese can be produced according to conventional methods (including the starting material) except that the step of adding TG for the reaction is incorporated according to any of the above-mentioned three processes.

When the solution is reacted with TG, a fixed reaction time and a fixed reaction temperature are needed. The usual production of cheese includes the rennetting step and the heating step which is called the "cooking step." Accordingly, when the second or third process is employed, there is no need for employing a new step of reacting the solution with TG. If the enzyme is added before or during the rennetting step or the cooking step, the effect of the present invention can be obtained satisfactorily during the rennetting step or the cooking step.

Since the present invention provides a process for producing cheese, namely, natural cheese, a step of acidifying the solution containing milk or the milk protein with a lactic-acid bacillus starter is conducted before or simultaneously with the addition of the milk clotting enzyme. A mold starter is used in producing some kinds of cheese.

When the first process of the present invention is conducted, a suitable reaction temperature and a suitable reaction time are needed after the addition of TG. When the reaction is conducted, for example, at from 10° to 40° C. for a reaction time of from 1 to 16 hours, the effect of the present invention is obtained sufficiently. When the temperature is lower than 10° C. or higher than 40° C., a suitable effect can be obtained by appropriately controlling the reaction time. Accordingly, the TG reaction conditions are not particularly limited.

Thus, a cheese curd having excellent firmness and body and other properties can be obtained in high yield by only incorporating the step of adding TG for the reaction into the conventional method of producing cheese without greatly changing the conventional starting materials, conventional additives and conventional steps which have been employed so far to produce cheese.

Cheese produced by the present invention can be the same as other kinds of cheese which are produced through traditional methods peculiar to them in terms of taste and texture, and it also has the same level of quality as the latter. The greatest advantage of the present invention is that cheese having the same quality can be produced in a larger amount from the same fixed amount of starting milk.

In addition, it is also possible to produce cheese having a novel taste and a novel texture which have not been found in conventional cheeses.

Cheddar cheese which is produced by the process of the present invention markedly exhibits the effect of the present invention. Cheddar cheese is a so-called hard cheese (water content of less than approximately 40%) which is currently the cheese that is produced in the largest amount outside of Japan. This is used as a starting material for process cheese, and the mild taste thereof is agreeable to the Japanese people in general.

The present invention which increases the yield of the curd for hard cheese such as cheddar cheese, which gives curd having excellent firmness, body and texture, and which provides high-quality cheese is industrially quite useful.

Further, when so-called soft cheese is produced in accordance with the present invention, the yield of curd is increased and the effect of preventing serum separation (referred to as "syneresis" or "water separation") is also provided. Soft fresh cheese such as quark or cottage cheese is difficult to keep in that it suffers water separation during storage. Japanese Laid-Open Patent Application (Kokai) No. 252,866/1993 describes a means for adding a stabilizer such that heat-sterilized fresh cheese does not cause aggregation and serum separation and has an excellent texture. The soft cheese which is produced by the process of the present invention is advantageous in that it does not cause serum separation during storage even if a stabilizer or the like is not added and it provides a smooth and comfortable texture.

The present invention will be illustrated specifically in referring to the following Examples.

EXAMPLE 1

(Production of cheddar cheese)

Starting milk (11 kg; fat content sterilized, cooled, and then heated up to 31° C. Then, 2.25 g of a mixed lactic acid starter (*S. lactis, S. Cremoris*, made by Chris. Hansen's Laboratories) were added thereto, and the mixture was kept at 31° C. for 60 minutes (step of fermenting lactic acid). When the step of fermenting lactic acid was conducted for 35 minutes, 0.72 ml of annatto food color were added. Five minutes later, 0.02% of calcium chloride were added. After the lactic acid fermentation step lasting 45 minutes, 2.25 ml of a calf rennet (single strength, made by Chris. Hansen's Laboratories) were added,and the mixture was allowed to stand for from 25 to 30 minutes to form a curd (rennetting step). The formation of the curd was confirmed, and the curd was cut (cutting step). After the completion of the cutting step, the product was allowed to heal for 5 minutes. The curd was gently stirred for 10 minutes, and heating was then started (cooking step) In the cooking step, first the temperature was elevated from 31° C. to 33° C., and the heating was conducted for 15 minutes, when TG was added. The amount of TG added was 10 U per gram of the protein (10 U/gp) in the starting milk. Subsequently, the temperature was elevated from 33° C. to 35° C. over a period of 15 minutes, and further from 35° C. to 38° C. over a period of 10 minutes. During the cooking step, the curd was slowly stirred so as not to crush the curd particles. Then, the stirring was continued at 38° C. for 15 minutes, and the curd was allowed to stand for from 5 to 10 minutes. Then, the whey was drained.

After the whey was drained, the resulting curd was cut into 6 inches wide pieces, and cut pieces were overlaid one over the other. These cut pieces were kept at from 37° C. to 38° C., and flipped every 15 minutes to prompt the drainage of the whey (cheddaring step). Thereafter, a step of milling the curd was conducted. The milled curd was gradually mixed with NaCl. At this time, NaCl was added for a total of three times such that the concentration of NaCl reached 4.5% of the curd. The curd was put in the hoop, pressed, and ripened to obtain a cheddar cheese product. A cheddar cheese product which was produced in the above-mentioned manner except that TG was not added was prepared as a control product.

After the pressing process, the weight of the curd and the dry weight of the curd were measured and compared. The organoleptical properties of the cheddar cheese was estimated after it had ripened for 30 days. The results are shown in Table 1.

TABLE 1

| Results of organoleptic evaluation | | |
|---|---|---|
| | Control product (without addition of TG) | TG 10 U/gp |
| Weight of the curd (g) | 878 | 1052 |
| Dry weight of the curd (g) | 518 | 616 |
| Solid content of the curd (g) | 59 | 59 |
| Yield of the curd (%) | 100 | 119 |

TABLE 1-continued

| Results of organoleptic evaluation | | |
|---|---|---|
| | Control product (without addition of TG) | TG 10 U/gp |
| (yield of the control curd is defined as 100%) | | |
| Condition of the block of cheese | excellent | excellent |
| Color | typical yellow of cheddar cheese | yellow approximately equal to that of the control product |
| Flavor, body and texture | suitable firmness, smooth texture | suitable firmness no bitterness |

Thus, in the cheddar cheese which was produced with the addition of 10 U/gp of TG, the yield of the curd was increased by approximately 20%. The TG product had sufficient firmness and good body as hard cheese, and it was equal to the control product with respect to flavor, taste and appearance. Thus, the product was acceptable.

EXAMPLE 2

Cheddar cheese was produced in the same manner as in Example 1 except that TG was added in excessive amounts of 50 U/gp and 100 U/gp.

When 100 U/gp of TG were added, a curd was obtained in which the weight of the pressed curd was 918 g and the dry weight of the curd was 552 g after the press process. On the other hand, when 50 U/gp of TG were added, a curd was obtained in which the weight of the pressed curd was 1,233 g and the dry weight of the curd was 757 g after the press process. When 100 U/gp of TG were added, the yield of the curd was higher than that in the control product, but it was lower than that given by the addition of 10 U/gp of TG and 50 U/gp of TG.

It proved to be important that TG be added at a concentration within the optimum range in order to obtain an increase in the yield of the curd of hard cheese. Further, the results of the organoleptic evaluation revealed that the cheddar cheese obtained by the addition of 100 U/gp of TG was a little bit inferior to that obtained by the addition of 10 U/gp and 50 U/gp of TG with respect to the body, texture and condition of the block of cheese.

EXAMPLE 3

(Production of Quark)

Quark is an unripened, soft-type fermented milk curd cheese which is produced in Germany, and elsewhere.

TG was added to 20 kg of starting milk (solids content of skim milk=8.2%; fat content=3.5%) at 25° C. The amount of TG was 5 unit per gram of the protein (5 U/gp) in the starting milk, and the reaction was conducted at 25° C. for 2 hours. After the completion of the TG reaction, the reaction mixture was heated up to 75° C. (TG deactivation), and cooled to 28° C. Then, 200 g of a mixed lactic acid starter and 0.01 g of a rennet were added, and the mixture was stirred.

The mixture was fermented to a pH of 4.7 at 28° C. for approximately 5 hours to form a curd. The curd was packed into a bag for filtration, and the whey was drained through cooling at from 5° to 10° C. to prepare quark. This quark was kneaded with the addition of 0.5% of NaCl to form a product.

As a control product, quark which was produced in the above-mentioned manner, except that TG was not added, was prepared. The results are shown in Table 2.

EXAMPLE 4

(Production of Quark)

Twenty kilograms of starting milk (solids content of skim milk=8.2%; fat content=3.5%) were sterilized and cooled. Subsequently, the temperature was elevated to 27° C., and 200 g of a mixed lactic-acid bacillus starter, 0.01 g of a rennet and 25 ml of a calcium chloride aqueous solution were added. At the same time, TG was added in an amount of 1 unit per gram of milk protein (1 U/gp), and the fermentation was conducted at 27° C. for 6 hours.

The curd formed was packed into a bag for filtration, and whey was drained through cooling at from 5° to 10° C. to prepare quark. This quark was kneaded with the addition of 0.5% of NaCl to form a product.

As a control product, quark which was produced in the above-mentioned manner, except that TG was not added, was prepared. The weight, dry weight and protein amount of the curd in the quark in Examples 3 and 4 were measured and compared. Further, the organoleptical properties of the quark were estimated. The results are shown in Table 2 below.

TABLE 2

| | Results of organoleptic evaluation | | | |
|---|---|---|---|---|
| | Example 3 Control product | Example 3 TG 1 U/gp | Example 4 Control product | Example 4 TG 5 U/gp |
| Weight of the curd (kg) | 3.02 | 3.62 | 3.43 | 3.88 |
| Dry weight of the curd (kg) | 0.69 | 0.69 | 0.74 | 0.76 |
| Solids content of the curd (%) | 22.8 | 19.1 | 21.6 | 19.6 |
| Yield of the curd (%) (yield of the control product is defined as 100%) | 100 | 120 | 100 | 113 |
| Color | white | white | white | white |
| Serum separation (after 3 days of production | +++ | − | ++ | − |
| Body and texture | suitable consistency, slightly dry and crumbling | suitable consistency, smooth texture | slightly dry and crumbling and rough texture | suitable consistency, good taste |

Thus, when quark was produced with the addition of TG, a large amount of the curd could be obtained. The quark had suitable consistency, creamy feeling and smooth texture, and the appearance thereof was excellent without causing serum separation. The quark obtained by the addition of TG was increased in water content, but was not watery, and had a rather mild, palatable taste.

Also in Example 3 and Example 4, the organoleptically excellent curd could be obtained in a larger amount than the curd of the control product, though there was a slight difference between Examples 3 and 4 in the improvement of the yield of the curd.

As mentioned above, the present invention can provide a cheese curd in a larger amount than that through the conventional method, by incorporating a very simple step of adding TG for a reaction in a fixed order into the process for producing so-called conventional natural cheese, including the step of adding a milk clotting enzyme as a cheese starter. Thus, the starting milk can be used effectively.

Further, the obtained cheese has a quality which is acceptable to consumers without impairing properties, such as flavor, texture and appearance peculiar to various kinds of cheese which are produced by traditional methods.

Obviously, numerous modifications and variations of the present invention are possible in light of the above teachings. It is therefore to be understood that within the scope of the appended claims, the invention may be practiced otherwise than as specifically described herein.

We claim:

1. A process for producing cheese, said process including a step of acidification in which a starter is added, said process comprising (1) adding a transglutaminase to a solution containing milk or a milk protein for a reaction at a first stage to obtain a mixture, (2) heat-treating the mixture at a second stage, (3) adding a milk clotting enzyme at a third stage to react the mixture with the milk clotting enzyme for a fixed period of time, and (4) recovering a cheese.

2. A process for producing cheese, said process including a step of acidification in which a starter is added, said process comprising (1) adding a milk clotting enzyme to a solution containing milk or a milk protein at a first stage to react the solution with the enzyme for a fixed period of time to obtain a mixture, (2) adding a transglutaminase to the mixture for a reaction at a second stage, and (3) recovering a cheese.

3. A process for producing cheese, said process including a step of acidification in which a starter is added, said process comprising adding a transglutaminase to a solution containing milk or a milk protein for a reaction and, at the same time, adding a milk clotting enzyme to the solution, and recovering a cheese.

4. The process of claim 1 wherein the amount of transglutaminase added is between 0.1 and 50 units per gram of the protein.

5. The process of claim 2 wherein the amount of transglutaminase added is between 0.1 and 50 units per gram of the protein.

6. The process of claim 3 wherein the amount of transglutaminase added is between 0.1 and 50 units per gram of the protein.

7. The process of claim 1 wherein the solution containing milk or the milk protein is acidified with a lactic acid starter either before or simultaneously with the addition of the milk clotting enzyme.

8. The process of claim 2 wherein the solution containing milk or the milk protein is acidified with a lactic acid starter either before or simultaneously with the addition of the milk clotting enzyme.

9. The process of claim 3 wherein the solution containing milk or the milk protein is acidified with a lactic acid starter either before or simultaneously with the addition of the milk clotting enzyme.

* * * * *

UNITED STATES PATENT AND TRADEMARK OFFICE
CERTIFICATE OF CORRECTION

PATENT NO. : 5,681,598
DATED: : OCTOBER 28, 1997
INVENTOR(S) : CHIYA KURAISHI, ET AL

It is certified that error appears in the above-identified patent and that said Letters patent is hereby corrected as shown below:

Column 7, line 23, after "step)" insert --.--.

Signed and Sealed this

Twenty-eighth Day of April, 1998

Attest:

BRUCE LEHMAN

Attesting Officer

Commissioner of Patents and Trademarks